(12) United States Patent
Weiman et al.

(10) Patent No.: US 11,771,564 B2
(45) Date of Patent: Oct. 3, 2023

(54) ARTICULATING AND EXPANDABLE VERTEBRAL IMPLANT

(71) Applicant: GLOBUS MEDICAL, INC., Audubon, PA (US)

(72) Inventors: Mark Weiman, Downingtown, PA (US); John Matthews, Philadelphia, PA (US); Kevin Gahman, Douglassville, PA (US); Colm McLaughlin, Glenside, PA (US); Chad Glerum, Pennsburg, PA (US); Adam Friedrich, Cinnaminson, NJ (US); Jason Gray, East Greenville, PA (US); Marcin Niemiec, Norristown, PA (US); Michael Harper, Pottstown, PA (US)

(73) Assignee: Globus Medical Inc., Audubon, PA (US)

( * ) Notice: Subject to any disclaimer, the term of this patent is extended or adjusted under 35 U.S.C. 154(b) by 228 days.

(21) Appl. No.: 17/073,564

(22) Filed: Oct. 19, 2020

(65) Prior Publication Data

US 2021/0030555 A1 Feb. 4, 2021

Related U.S. Application Data

(60) Division of application No. 15/693,695, filed on Sep. 1, 2017, now Pat. No. 10,842,640, which is a
(Continued)

(51) Int. Cl.
*A61F 2/44* (2006.01)
*A61F 2/46* (2006.01)
*A61F 2/30* (2006.01)

(52) U.S. Cl.
CPC ............ *A61F 2/442* (2013.01); *A61F 2/4455* (2013.01); *A61F 2/4611* (2013.01); *A61F 2/4603* (2013.01);
(Continued)

(58) Field of Classification Search
CPC ...... A61F 2/442; A61F 2/4455; A61F 2/4611; A61F 2002/30405; A61F 2002/30538;
(Continued)

(56) References Cited

U.S. PATENT DOCUMENTS 4,349,921 A 9/1982 Kuntz
4,599,086 A 7/1986 Doty
(Continued)

FOREIGN PATENT DOCUMENTS

CA 2088066 A1 1/1992
DE 4012622 C1 7/1991
(Continued)

*Primary Examiner* — Nicholas J Plionis (57) ABSTRACT

An implant is insertable in the joint space to separate bones of the joint. The implant has two endplates each configured to engage a separate articulating bone of the joint, and a threaded member positioned between the two endplates and configured to increase the space between the two endplates when the threaded member is rotated. A rotatable gear is engaged with the threaded member, and is engageable with a rotating gear of a connected implantation tool, so that rotation of the gear on the tool causes rotation of the threaded member and expansion of the implant to separate the bones. Connector portions on the tool and the implant may be rotated together to securely engage the implant and the tool so that the gears of the tool and the implant can be rotated using an actuator outside of the body, when the implant is inside the body.

11 Claims, 5 Drawing Sheets

Related U.S. Application Data continuation of application No. 13/768,511, filed on Feb. 15, 2013, now Pat. No. 9,782,265.

(52) U.S. Cl.
CPC .............. *A61F 2002/3037* (2013.01); *A61F 2002/30092* (2013.01); *A61F 2002/30131* (2013.01); *A61F 2002/30156* (2013.01); *A61F 2002/30181* (2013.01); *A61F 2002/30266* (2013.01); *A61F 2002/30405* (2013.01); *A61F 2002/30523* (2013.01); *A61F 2002/30538* (2013.01); *A61F 2002/30556* (2013.01); *A61F 2002/30579* (2013.01); *A61F 2002/30601* (2013.01); *A61F 2002/30797* (2013.01); *A61F 2002/4627* (2013.01)

(58) Field of Classification Search
CPC .. A61F 2002/30556; A61F 2002/30579; A61F 2002/30601; A61F 2002/4627
See application file for complete search history.

(56) References Cited

U.S. PATENT DOCUMENTS

| | | | |
|---|---|---|---|
| 4,863,476 A | 9/1989 | Shepperd | |
| 4,863,477 A | 9/1989 | Monson | |
| 5,123,926 A | 6/1992 | Pisharodi | |
| 5,290,312 A | 3/1994 | Kojimoto et al. | |
| 5,306,310 A | 4/1994 | Siebels | |
| 5,375,823 A | 12/1994 | Navas | |
| 5,390,683 A | 2/1995 | Pisharodi | |
| 5,522,899 A | 6/1996 | Michelson | |
| 5,534,030 A | 7/1996 | Navarro et al. | |
| 5,554,191 A | 9/1996 | Lahille et al. | |
| 5,571,192 A | 11/1996 | Schonhoffer | |
| 5,645,596 A | 7/1997 | Kim | |
| 5,653,763 A | 8/1997 | Errico et al. | |
| 5,665,122 A * | 9/1997 | Kambin | A61F 2/4611 606/279 |
| 5,676,701 A | 10/1997 | Yuan et al. | |
| 6,039,761 A | 3/2000 | Li et al. | |
| 6,045,579 A | 4/2000 | Hochschuler et al. | |
| 6,080,193 A | 6/2000 | Hochschuler et al. | |
| 6,099,531 A | 8/2000 | Bonutti | |
| 6,102,950 A * | 8/2000 | Vaccaro | A61F 2/4637 606/247 |
| 6,126,689 A | 10/2000 | Brett | |
| 6,176,882 B1 | 1/2001 | Biedermann et al. | |
| 6,258,125 B1 | 7/2001 | Paul et al. | |
| 6,443,989 B1 * | 9/2002 | Jackson | A61F 2/447 606/247 |
| 6,558,423 B1 | 5/2003 | Michelson | |
| 6,562,074 B2 | 5/2003 | Gerbec et al. | |
| 6,576,016 B1 | 6/2003 | Hochschuler et al. | |
| 6,554,863 B2 | 8/2003 | Paul et al. | |
| 6,641,614 B1 | 11/2003 | Wagner et al. | |
| 6,648,917 B2 | 11/2003 | Gerbec et al. | |
| 6,666,891 B2 | 12/2003 | Boehm, Jr. et al. | |
| 6,692,495 B1 | 2/2004 | Zacouto | |
| 6,706,070 B1 | 3/2004 | Wagner et al. | |
| 6,752,832 B2 | 6/2004 | Ulrich | |
| 6,814,756 B1 | 11/2004 | Michelson | |
| 6,821,298 B1 * | 11/2004 | Jackson | A61F 2/4455 623/17.11 |
| 6,830,589 B2 | 12/2004 | Erickson | |
| 6,849,093 B2 | 2/2005 | Michelson | |
| 6,852,129 B2 | 2/2005 | Gerbec et al. | |
| 6,863,673 B2 | 3/2005 | Gerbec et al. | |
| 6,881,228 B2 | 4/2005 | Zdeblick et al. | |
| 7,018,415 B1 | 3/2006 | McKay | |
| 7,070,598 B2 | 7/2006 | Lim et al. | |
| 7,204,853 B2 | 4/2007 | Gordon | |
| 7,217,291 B2 | 5/2007 | Zucherman et al. | |
| 7,282,063 B2 | 10/2007 | Cohen et al. | |
| 7,316,714 B2 | 1/2008 | Gordon | |
| 7,473,276 B2 | 1/2009 | Aebi et al. | |
| 7,547,325 B2 | 6/2009 | Biedermann et al. | |
| 7,621,953 B2 | 11/2009 | Braddock, Jr. et al. | |
| 7,641,693 B2 | 1/2010 | Gutlin et al. | |
| 7,682,396 B2 | 3/2010 | Beaurain et al. | |
| 7,749,270 B2 | 7/2010 | Peterman | |
| 7,753,958 B2 | 7/2010 | Gordon | |
| 7,771,473 B2 | 8/2010 | Thramann | |
| 7,780,732 B2 | 8/2010 | Abernathie | |
| 7,799,081 B2 | 9/2010 | McKinley | |
| 7,815,683 B2 | 10/2010 | Melkent et al. | |
| 7,837,734 B2 | 11/2010 | Zucherman et al. | |
| 7,875,078 B2 | 1/2011 | Wysocki et al. | |
| 7,901,409 B2 | 3/2011 | Canaveral et al. | |
| 7,909,869 B2 | 3/2011 | Gordon | |
| 7,951,199 B2 | 5/2011 | Miller | |
| 7,985,256 B2 | 7/2011 | Grotz et al. | |
| 8,062,375 B2 | 11/2011 | Glerum | |
| 8,070,813 B2 | 12/2011 | Grotz et al. | |
| 8,123,810 B2 | 2/2012 | Gordon | |
| 8,137,405 B2 | 3/2012 | Kostuik et al. | |
| 8,192,495 B2 | 6/2012 | Simpson et al. | |
| 8,303,663 B2 | 11/2012 | Jimenez et al. | |
| 8,377,140 B2 | 2/2013 | DeFalco et al. | |
| 8,394,129 B2 | 3/2013 | Lopez et al. | |
| 8,394,143 B2 | 3/2013 | Grotz et al. | |
| 8,435,296 B2 | 5/2013 | Kadaba et al. | |
| 8,454,695 B2 | 6/2013 | Grotz et al. | |
| 8,647,386 B2 | 2/2014 | Gordon | |
| 8,696,751 B2 | 4/2014 | Ashley et al. | |
| 8,771,360 B2 | 7/2014 | Jimenez et al. | |
| 8,894,710 B2 | 11/2014 | Simpson et al. | |
| 8,932,355 B2 | 1/2015 | Grotz et al. | |
| 8,940,049 B1 | 1/2015 | Jimenez et al. | |
| 8,956,413 B2 | 2/2015 | Ashley et al. | |
| 8,992,620 B2 | 3/2015 | Ashley et al. | |
| 9,028,550 B2 | 5/2015 | Shulock et al. | |
| 9,358,125 B2 | 6/2016 | Jimenez et al. | |
| 9,532,883 B2 | 1/2017 | McLuen et al. | |
| 9,622,878 B2 | 4/2017 | Grotz | |
| 2002/0045945 A1 | 4/2002 | Liu | |
| 2002/0068976 A1 | 6/2002 | Jackson | |
| 2002/0068977 A1 | 6/2002 | Jackson | |
| 2003/0176926 A1 | 9/2003 | Boehm et al. | |
| 2004/0030387 A1 | 2/2004 | Landry et al. | |
| 2004/0049271 A1 | 3/2004 | Biedermann | |
| 2004/0054412 A1 | 3/2004 | Gerbec et al. | |
| 2004/0087947 A1 | 5/2004 | Lim et al. | |
| 2004/0153065 A1 | 8/2004 | Lim | |
| 2005/0021041 A1 | 1/2005 | Michelson | |
| 2005/0021145 A1 | 1/2005 | de Villiers et al. | |
| 2005/0033432 A1 | 2/2005 | Gordon | |
| 2005/0080422 A1 | 4/2005 | Otte et al. | |
| 2005/0113916 A1 | 5/2005 | Branch | |
| 2005/0149188 A1 | 7/2005 | Cook | |
| 2005/0171541 A1 | 8/2005 | Boehm | |
| 2005/0251258 A1 | 11/2005 | Jackson | |
| 2005/0273171 A1 | 12/2005 | Gordon | |
| 2005/0273174 A1 | 12/2005 | Gordon | |
| 2005/0278026 A1 | 12/2005 | Gordon | |
| 2005/0283244 A1 | 12/2005 | Gordon | |
| 2005/0283245 A1 | 12/2005 | Gordon | |
| 2006/0004453 A1 | 1/2006 | Bartish, Jr. et al. | |
| 2006/0015184 A1 | 1/2006 | Winterbottom et al. | |
| 2006/0058878 A1 | 3/2006 | Michelson | |
| 2006/0084986 A1 | 4/2006 | Grinberg et al. | |
| 2006/0122701 A1 | 6/2006 | Kister | |
| 2006/0129244 A1 | 6/2006 | Ensign | |
| 2006/0142859 A1 | 6/2006 | Mcluen | |
| 2006/0149385 A1 | 7/2006 | Mckay | |
| 2006/0195192 A1 | 8/2006 | Gordon et al. | |
| 2006/0229729 A1 | 10/2006 | Gordon | |
| 2006/0241770 A1 | 10/2006 | Rhoda et al. | |
| 2006/0253201 A1 | 11/2006 | Mcluen | |
| 2007/0043442 A1 | 2/2007 | Abernathie | |
| 2007/0050030 A1 | 3/2007 | Kim | |
| 2007/0050032 A1 | 3/2007 | Gittings et al. | |
| 2007/0055377 A1 | 3/2007 | Hanson et al. | |

(56) References Cited

U.S. PATENT DOCUMENTS

| | | |
|---|---|---|
| 2007/0191951 A1 | 8/2007 | Branch |
| 2007/0255415 A1 | 11/2007 | Edie et al. |
| 2007/0270963 A1 | 11/2007 | Melkent et al. |
| 2007/0270968 A1 | 11/2007 | Baynham |
| 2008/0021559 A1 | 1/2008 | Thramann |
| 2008/0065222 A1 | 3/2008 | Hamada |
| 2008/0114467 A1 | 5/2008 | Capote et al. |
| 2008/0140207 A1 | 6/2008 | Olmos et al. |
| 2008/0147194 A1 | 6/2008 | Grotz et al. |
| 2008/0161933 A1 | 7/2008 | Grotz et al. |
| 2008/0167657 A1 | 7/2008 | Greenhalgh |
| 2008/0183204 A1 | 7/2008 | Greenhalgh et al. |
| 2008/0221694 A1 | 9/2008 | Warnick et al. |
| 2008/0275455 A1 | 11/2008 | Berry et al. |
| 2008/0281346 A1 | 11/2008 | Greenhalgh et al. |
| 2008/0288073 A1 | 11/2008 | Renganath et al. |
| 2008/0300598 A1 | 12/2008 | Barreiro et al. |
| 2008/0306488 A1 | 12/2008 | Altarac et al. |
| 2008/0319487 A1 | 12/2008 | Fielding et al. |
| 2008/0319549 A1 | 12/2008 | Greenhalgh et al. |
| 2009/0024217 A1 | 1/2009 | Levy et al. |
| 2009/0062833 A1 | 3/2009 | Song |
| 2009/0076616 A1 | 3/2009 | Duggal et al. |
| 2009/0125062 A1 | 5/2009 | Amin |
| 2009/0149956 A1 | 6/2009 | Greenhalgh et al. |
| 2009/0149959 A1 | 6/2009 | Conner et al. |
| 2009/0204218 A1 | 8/2009 | Richelsoph |
| 2009/0222100 A1 | 9/2009 | Cipoletti et al. |
| 2009/0240334 A1 | 9/2009 | Richelsoph |
| 2009/0270989 A1 | 10/2009 | Conner et al. |
| 2009/0281628 A1 | 11/2009 | Oglaza et al. |
| 2009/0292361 A1 | 11/2009 | Lopez |
| 2009/0299478 A1 | 12/2009 | Carls et al. |
| 2009/0312763 A1 | 12/2009 | McCormack |
| 2010/0049324 A1 | 2/2010 | Valdevit |
| 2010/0070041 A1 | 3/2010 | Peterman |
| 2010/0082109 A1 | 4/2010 | Greenhalgh et al. |
| 2010/0145455 A1 | 6/2010 | Simpson et al. |
| 2010/0179657 A1 | 7/2010 | Greenhalgh et al. |
| 2010/0211176 A1 | 8/2010 | Greenhalgh |
| 2010/0222816 A1 | 9/2010 | Gabelberger et al. |
| 2010/0286783 A1 | 11/2010 | Lechmann et al. |
| 2011/0035011 A1 | 2/2011 | Cain |
| 2011/0093074 A1 | 4/2011 | Glerum et al. |
| 2011/0160861 A1 | 6/2011 | Jimenez et al. |
| 2011/0172774 A1 | 7/2011 | Varela |
| 2011/0178598 A1* | 7/2011 | Rhoda .................. A61F 2/4465 623/17.16 |
| 2011/0276142 A1 | 11/2011 | Niemiec et al. |
| 2011/0301713 A1 | 12/2011 | Theofilos |
| 2011/0319997 A1 | 12/2011 | Glerum et al. |
| 2012/0035729 A1 | 2/2012 | Glerum et al. |
| 2012/0059470 A1 | 3/2012 | Weiman |
| 2012/0059472 A1 | 3/2012 | Weiman |
| 2012/0109308 A1 | 5/2012 | Lechmann et al. |
| 2012/0130496 A1 | 5/2012 | Duffield et al. |
| 2012/0165945 A1 | 6/2012 | Hansell et al. |
| 2012/0185049 A1 | 7/2012 | Varela |
| 2012/0209384 A1 | 8/2012 | Arnold et al. |
| 2012/0209386 A1 | 8/2012 | Triplett et al. |
| 2012/0215313 A1 | 8/2012 | Saidha et al. |
| 2012/0226357 A1 | 9/2012 | Varela |
| 2012/0265303 A1 | 10/2012 | Refai et al. |
| 2012/0265309 A1 | 10/2012 | Glerum et al. |
| 2012/0277861 A1 | 11/2012 | Steele et al. |
| 2012/0277870 A1 | 11/2012 | Wolters et al. |
| 2012/0323329 A1 | 12/2012 | Jimenez et al. |
| 2012/0330426 A1 | 12/2012 | McLaughlin et al. |
| 2013/0023993 A1 | 1/2013 | Weiman |
| 2013/0023994 A1 | 1/2013 | Glerum |
| 2013/0158663 A1 | 6/2013 | Miller et al. |
| 2013/0158669 A1 | 6/2013 | Sungarian et al. |
| 2013/0197647 A1 | 8/2013 | Wolters et al. |
| 2013/0211526 A1 | 8/2013 | Alheidt et al. |
| 2013/0274883 A1 | 10/2013 | McLuen et al. |
| 2014/0067071 A1 | 3/2014 | Weiman et al. |
| 2014/0088714 A1 | 3/2014 | Miller et al. |
| 2014/0163683 A1 | 6/2014 | Seifert et al. |
| 2015/0066145 A1 | 3/2015 | Rogers et al. |
| 2015/0088258 A1 | 3/2015 | Jimenez et al. |
| 2015/0134064 A1 | 5/2015 | Grotz et al. |
| 2015/0216676 A1 | 8/2015 | Shulock et al. |
| 2015/0289988 A1 | 10/2015 | Ashley et al. |
| 2015/0374508 A1 | 12/2015 | Sandul |
| 2016/0166396 A1 | 6/2016 | McClintock |
| 2016/0324654 A1 | 11/2016 | Loebl et al. |
| 2017/0100258 A1 | 4/2017 | Jimenez et al. |
| 2017/0119543 A1 | 5/2017 | Dietzel et al. |

FOREIGN PATENT DOCUMENTS

| | | |
|---|---|---|
| DE | 4327054 C1 | 4/1995 |
| EP | 0576379 B1 | 6/1993 |
| EP | 0610837 B1 | 7/1994 |
| EP | 3111896 A1 | 1/2017 |
| FR | 2794968 A1 | 12/2000 |
| JP | 2000-513263 A | 10/2000 |
| JP | 2011520580 A | 7/2011 |
| KR | 200290058 Y1 | 9/2002 |
| WO | 9201428 A1 | 2/1992 |
| WO | 9525485 A1 | 9/1995 |
| WO | 1999042062 A1 | 8/1999 |
| WO | 1999066867 A1 | 12/1999 |
| WO | 2002045625 A1 | 6/2002 |
| WO | 2004019829 A1 | 3/2004 |
| WO | 2004069033 A2 | 8/2004 |
| WO | 2006045094 A2 | 4/2006 |
| WO | 2006047587 A2 | 5/2006 |
| WO | 2006113080 A2 | 10/2006 |
| WO | 2008044057 A1 | 4/2008 |
| WO | 2008134515 A1 | 11/2008 |
| WO | 2009114381 A1 | 9/2009 |
| WO | 2010103344 A1 | 9/2010 |
| WO | 2012031267 A1 | 3/2012 |
| WO | 2013023096 | 2/2013 |
| WO | 2015009793 A1 | 1/2015 |

* cited by examiner

ARTICULATING AND EXPANDABLE VERTEBRAL IMPLANT

CROSS-REFERENCE TO RELATED APPLICATIONS

The present application is a divisional patent application of U.S. patent application Ser. No. 15/693,695 filed on Sep. 1, 2017, which is a continuation patent application of U.S. patent application Ser. No. 13/768,511, filed on Feb. 15, 2013 (published as U.S. Patent Publication No. 2014-0316522), which is hereby incorporated by reference in its entirety.

FIELD OF THE INVENTION

This invention relates to stabilizing adjacent vertebrae of the spine by inserting an intervertebral spacer, and more particularly an intervertebral spacer that is adjustable in height, and a tool therefore.

BACKGROUND OF THE INVENTION

The vertebral or spinal column (spine, backbone) is a flexible assembly of vertebrae stacked on top of each other extending from the skull to the pelvic bone which acts to support the axial skeleton and to protect the spinal cord and nerves. The vertebrae are anatomically organized into four generalized body regions identified as cervical, thoracic, lumbar, and sacral; the cervical region including the top of the spine beginning in the skull, the thoracic region spanning the torso, the lumbar region spanning the lower back, and the sacral region including the base of the spine ending with connection to the pelvic bone. With the exception of the first two cervical vertebrae, cushion-like discs separate adjacent vertebrae, i.e. intervertebral discs.

The stability of the vertebral column during compression and movement is maintained by the intervertebral discs. Each disc includes a gel-like center surrounded by a fibrous ring. The gel-like center, i.e. nucleus pulposus, provides strength such that the disc can absorb and distribute external loads and contains a mixture of type II-collagen dispersed in a proteoglycan matrix. The fibrous ring, or annulus fibrosus, provides stability during motion and contains laminated rings of type-I collagen. Thus, the annulus fibrosis and the nucleus pulposus are interdependent, as the annulus fibrosis contains the nucleus pulposus in place and the nucleus pulposus aligns the annulus fibrosus to accept and distribute external loads. The integrity of the composition and structure of the intervertebral disc is necessary to maintain normal functioning of the intervertebral disc.

Many factors can adversely alter the composition and structure of the intervertebral disc, such as normal physiological aging, mechanical injury/trauma, and/or disease, resulting in impairment or loss of disc function. For example, the content of proteoglycan in the nucleus pulposus declines with age, thus, it follows that the ability of the nucleus pulposus to absorb water concurrently declines. Therefore, in normal aging the disc progressively dehydrates, resulting in a decrease in disc height and possible de-lamination of the annulus fibrosus. Mechanical injury can tear the annulus fibrosis allowing the gel-like material of the nucleus pulposus to extrude into the spinal canal and compress neural elements. Growth of a spinal tumor can impinge upon the vertebrae and/or disc potentially compressing nerves.

Bones of the spine, and bony structures, generally, are susceptible to a variety of weaknesses that can affect their ability to provide support and structure. Weaknesses in bony structures have numerous potential causes, including degenerative diseases, tumors, fractures, and dislocations. Advances in medicine and engineering have provided doctors with a plurality of devices and techniques for alleviating or curing these weaknesses.

In some cases, the spinal column, in particular, requires additional support in order to address such weaknesses. One technique for providing support is to insert a spacer between adjacent vertebrae.

SUMMARY OF THE INVENTION

In accordance with an embodiment of the disclosure, an implant for separating bones of a joint comprises at least two endplates, two of the at least two endplates each configured to engage a separate articulating bone of the joint; at least one threaded member configured to increase a space between the two endplates when the at least one threaded member is rotated; a rotatable gear engageable with a rotating gear of an implantation tool when the implantation tool is connected to the engagement bore, the rotatable gear configured to rotate the at least one threaded member; and an engagement bore configured to be releaseably and securely connectable to a rotating connector portion of an implantation tool.

In various embodiments thereof, the threaded member has the form of a threaded shaft; the threaded member has the form of a threaded cone; the threaded cone has a geared face; and the implant further includes at least one ramped surface formed upon at least one of the two endplates, the at least one ramped surface mateable with the cone to be resiliently displaced to change a height dimension of the implant when the cone is moved against the at least one ramped surface.

In other embodiments thereof, the implant further includes at least one lift ramp connected to the threaded member to move linearly as the threaded member is rotated; and at least one expansion ramp located upon at least one of the two endplates, the at least one expansion ramp mateable with the at least one lift ramp to cause movement of the at least one expansion ramp upon which the at least one expansion ramp is located when the lift ramp is moved.

In other embodiments thereof, the engagement bore is configured to form an angle between a maximum longitudinal axis of the implant and a maximum longitudinal axis of a connected implantation tool, when the implantation tool is connected to the implant; the at least one threaded member and the at least one rotatable gear rotate about a common axis; and the at least one threaded member and the at least one rotatable gear rotate about separate axes.

In a yet further embodiment thereof, the implant further includes a gear rack extending from a first of the two endplates; a pinion is rotatably connected to a second of the two endplates, meshed with the rack, the pinion thereby rotated when the first and second endplates are moved relatively apart; a strut pivotally and eccentrically connected to the pinion at a first end, and connected to a carriage at a second opposite end, the strut configured to move the carriage substantially linearly as the pinion is rotated; at least one lift ramp extending from the carriage; and at least one expansion ramp extending from at least one of the at least two endplates, the at least one expansion ramp mateable with the at least one lift ramp, whereby when the carriage is moved linearly, the at least one lift ramp is moved against the at least one expansion ramp to cause movement of the at least one endplate from which the at least one expansion ramp extends, to change a dimensional height of the implant. In an embodiment, the threaded member has the form of a threaded cone, the implant further including at least one ramped surface formed upon at least one of the two endplates, the at least one ramped surface mateable with the cone to be resiliently displaced to change a height dimension of the implant when the cone is moved against the at least one ramped surface, the displacement of the at least one endplate operable to move the rack.

In further embodiments thereof, two of the at least two threaded members are threaded collars having an internally disposed thread, and an external gear face, the external gear face of both threaded members meshed, whereby rotation of one threaded member causes a rotation of the other threaded member; and the implant further includes two expansion shafts connected to at least one of the at least two endplates, the two expansion shafts each having externally disposed threads mated with an internally disposed thread of one of the two threaded collars, whereby rotation of one of the two threaded collars causes movement of both of the two expansion shafts.

In another embodiment of the disclosure, an implant for separating bones of a joint comprises a first endplate configured to engage a first articulating bone of a joint; a second endplate configured to engage a second, different articulating bone of a joint relative to the first endplate; a base supporting the first endplate; a threaded shaft having first and second shaft ends, the threaded shaft connected to the second endplate at the first shaft end; a rotatable gear rotatably connected to the base, and connected to the second shaft end, the rotatable gear configured to move the threaded shaft when the rotatable gear is rotated, to thereby increase a distance between the first and second endplates; and an engagement bore configured to be releaseably and securely connectable to a rotating connector portion of an implantation tool.

In various embodiments thereof, the implant further includes a lift ramp extending from the second shaft end, and an expansion ramp extending from the second endplate; the engagement bore configured to form an angle between a maximum longitudinal axis of the implant and a maximum longitudinal axis of a connected implantation tool, when the implantation tool is connected to the implant; the rotatable gear located at an end of the implant, the rotatable gear configured to be rotatable once the implant has been implanted between bones of the joint; and, the at least one threaded member and the at least one rotatable gear rotate about a common axis.

In a yet further embodiment of the disclosure, a system for separating bones of a joint comprises an implantation tool including a connector end having a tool rotatable gear and a rotatable tool connector member distinct from the tool rotatable gear; and an implant including—at least two endplates, two of the at least two endplates configured to engage separate articulating bone of a joint; at least one threaded member configured to increase a space between the two endplates when the at least one threaded member is rotated; an implant connector member mateable with the tool connector member to securely and releaseably connect the implant to the tool when the tool connector member is rotated; and an implant rotatable gear configured to rotate at least one of the at least one threaded member, the implant rotatable gear engageable with the tool rotatable gear when the implant and the tool are connected using the implant connector and tool connector, the tool rotatable gear thereby configured to rotate the implant rotatable gear to rotate at least one of the at least one threaded member.

In an embodiment thereof, the tool further includes a rotatable shaft connected to the tool rotatable gear at one end, and an actuator at an opposite end, the actuator rotatable outside of the body when the tool rotatable gear is engaged with the implant rotatable gear and the implant is positioned between bones of the joint.

BRIEF DESCRIPTION OF THE DRAWINGS

A more complete understanding of the disclosure, and the attendant advantages and features thereof, will be more readily understood by reference to the following detailed description when considered in conjunction with the accompanying drawings, in which.

DETAILED DESCRIPTION OF THE INVENTION

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language).

Figure 1:
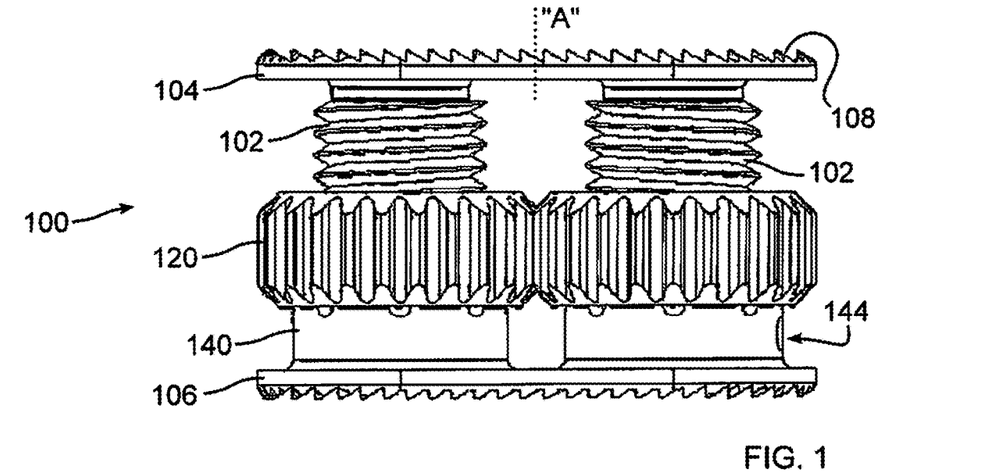
FIG. 1 depicts a spacer implant of the disclosure, including two threaded shafts and two threaded collars which have been rotated to increase a height of the implant.
Figure 2:
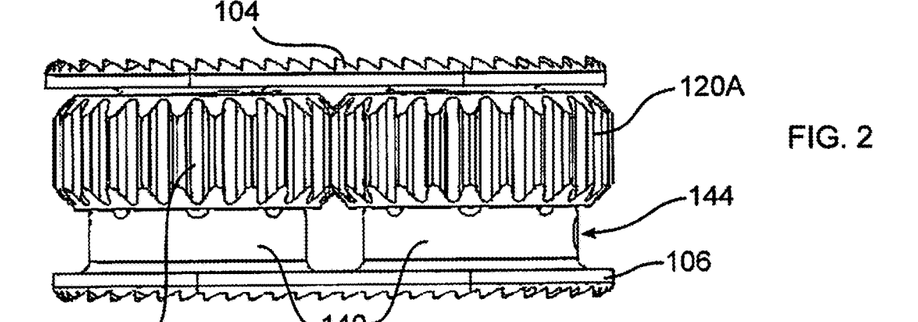
FIG. 2 depicts the implant of FIG. 1, the collars rotated to decrease a height of the implant.
Figure 3:
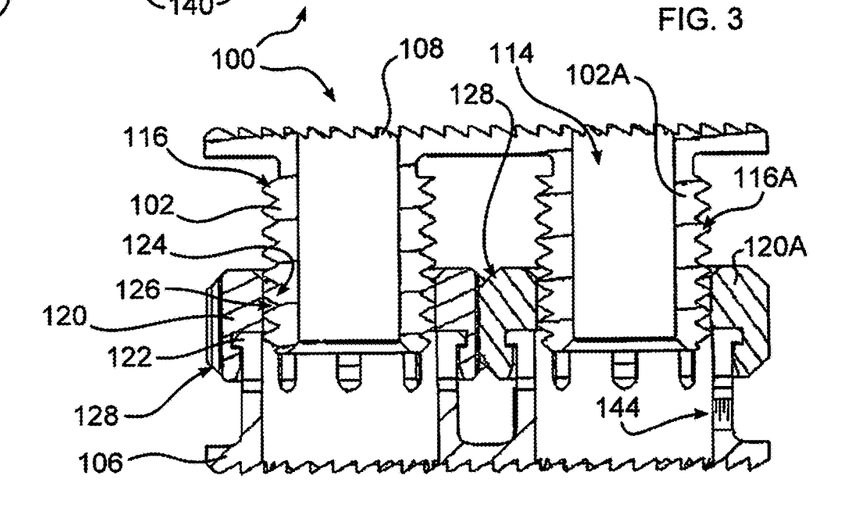
FIG. 3 depicts a cross-section through a center of the implant of FIG. 1.

With reference to FIGS. 1-3, the disclosure provides an expandable implant 100 having an adjustable height. The implant is inserted between two adjacent bony surfaces to facilitate separation of the bones, and if desired, can promote the fusion of the bony surfaces. Although intended to be useful with any adjacent bony surface in which fusion is desired, the implant is advantageously applied to insertion between two adjacent vertebral bodies in any section of the spine, including the cervical, thoracic, lumbar, and sacral vertebral sections. More than one implant 100 may be implanted within the body, for example between successive or separated vertebrae. The use of multiple implants is particularly advantageous for patients whose back pain is not limited to a localized area, or for patients whose localized damage has progressed to other areas of the spine.

The implant and methods for its insertion can be used in a treatment protocol for any of a wide variety of conditions in a patient involving diseased or damaged bony structures. The patient can be a human being. Additionally, it is contemplated that the implant may be useful in veterinary science for any animal having adjacent bony structures to be fused. The implant can collapse, for example, to approximately one half of an expanded size. When in this collapsed configuration, the implant can be inserted into a space through a small incision and narrow pathways, using appropriate minimally-invasive techniques, and can be positioned within the space between adjacent bones, and there expanded to a desired therapeutic height. The incision may be short, for example about one inch in length, which is smaller than the implant in an expanded configuration. If the desired position and/or expansion are not achieved, the implant can be collapsed, repositioned, and rexpanded in situ.

Although the implant is exemplified herein for use in the spine, the implant is contemplated for fusion of any bony structures. While the implants are described herein using several varying embodiments, the implants are not limited to these embodiments. An element of one embodiment may be used in another embodiment, or an embodiment may not include all described elements.

Operation of implant 100 is described in greater detail below. One or more threaded shafts 102 support an endplate 104, and can be provided with tooth or other projections 108 which engage bone of the patient. A threaded collar 120 is rotatably affixed to a base 140 by a flanged engagement 122 (FIG. 3), which maintains an axial alignment of collar 120 upon base 140. An opposing endplate 106 is affixed to base 140. An internal bore 124 of collar 120 has threads 126 which mate with threads 116 of shaft 102. As collar 120 is rotated, engagement of threads 126 and 116 cause shaft 102 to ascend or descend within collar bore 124 of collar 120.

While the embodiments illustrated herein depict unitary or monolithic endplates, it should be understood that endplates of the disclosure may each be formed of multiple portions to reduce a compressed or unexpanded profile of the implant, to better conform to a surface of bones of the joint, and or to enable expansion of different portions of an endplate differently, for the therapeutic benefit of the patient. For example, dashed line "A" of FIG. 1 indicates one possible location for a separation of endplate 104 into two portions. Variable expansion of each resultant portion can be expanded differently relative to the other, for example, by forming a different pitch upon each of threaded shafts 102.

To cause shaft 102 to move axially and not radially, rotation of shaft 102 relative to base 140 is prevented. In the example shown, shaft 102 engages endplate 104, which cannot rotate due to engagement with endplate 104 and an adjacent shaft 102. However, in a configuration with a single shaft 102, rotation can be prevented using mating axial splines extending between shaft 102 and base 140, or other moveable connection between shaft 102 and base 140.

In the embodiment of FIGS. 1-3, collar 120 and 120A are mutually engaged by gear teeth 128 formed on an exterior of collars 120, 120A. Due to this gear engagement, collar 120A rotates in an opposite direction to collar 120. To cause shafts 102 and 102A to move axially in the same direction during rotation of collars 120, 120A, shaft 102A has a reverse thread with respect to shaft 102. In an alternative embodiment, an idler wheel (not shown), is interposed between gear engagements 128, to produce a like rotational direction of collars 120, 120A, and shafts 102, 102A. Shaft 102 can be provided with a bore 114, cooperative with collar bore 124, to admit the growth of bone or other tissue through implant 100, to promote bone fusion.

FIGS. 1 and 3 illustrate implant 100 in expanded states, and FIG. 2 illustrates implant 100 in a collapsed state, in which state implant 100 is advantageously inserted into the body. As collars 120, 120A are mutually engaged, it is only necessary to access and rotate one of the collars in order to rotate both collars within the body. This is advantageous when implant 100 is inserted between vertebrae, because only one collar is accessible through an opening formed in the annulus, the other collar typically surrounding by remaining tissue. While it may be possible, in some instances, to rotate the exposed collar 120 with fingers, or a drift, neither may be an ideal method due to space limitations and patient safety, particularly where it is necessary to avoid delicate structures adjacent to the exposed collar. Implant 100 provides an ability to adjust a height of the spacer to any desired height between a minimum, collapsed height, and a maximum, fully expanded height.

Figures 4, 5:
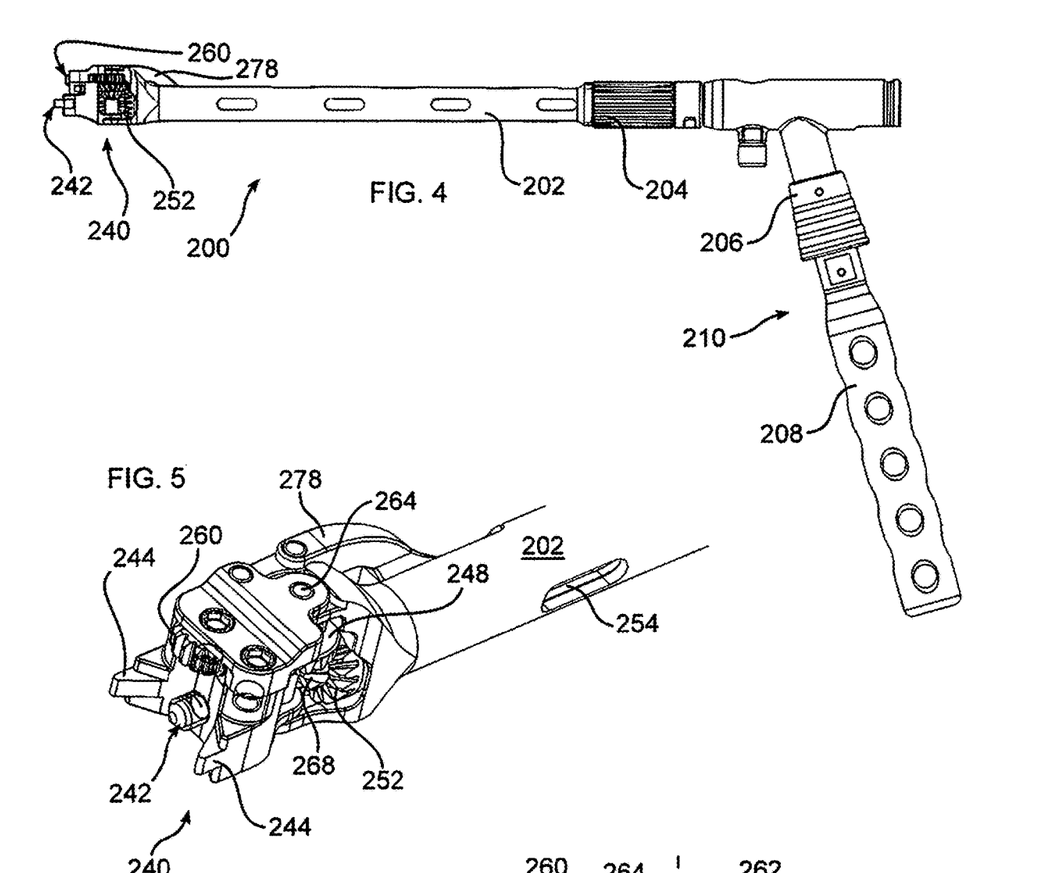
FIG. 4 depicts an implantation deployment tool of the disclosure for inserting and expanding, within the body, an implant of the disclosure.
FIG. 5 depicts an enlarged view of a connector end of the tool of FIG. 4.
Figure 6:
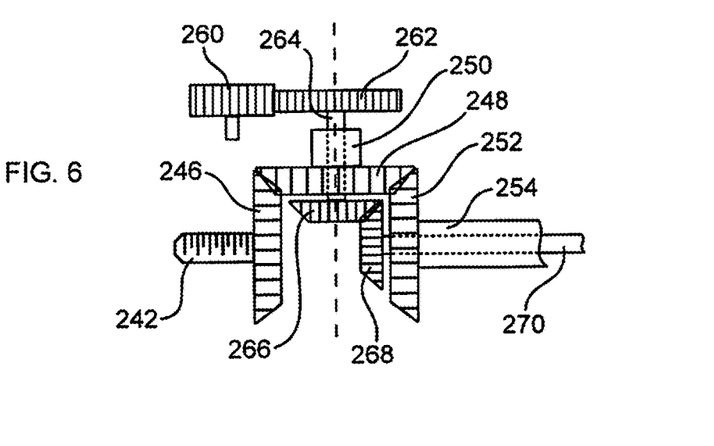
FIG. 6 depicts a schematic view of one configuration of the connector end of FIG. 5.

Accordingly, with reference to FIGS. 4-6, an insertion and deployment tool 200 can be used to insert implant 100, and or to rotate collar 120 to expand implant 100. Tool 200 includes an actuating connector 240, an extension shaft 202, actuators 204, 206, and 208, and a handle 210. In use, a medical practitioner grasps the handle and or extension shaft 202, connects an implant 100, as described further below, and inserts extension shaft 202, together with implant 100, into a deployment location within the patient's body. While actuators 204, 206, and 208 are illustrated as rotatable rings or a rotatable handle, it should be understood that other actuator styles can be provided in accordance with the disclosure, including trigger style actuators, or actuators driven by an external power source, including electricity or a pressurized fluid, for example.

Connector 240 includes an implant coupling screw 242 which, cooperative with engagement extensions 244, securely and releasably connects implant 100 to tool 200. Implant 100 includes one or more of a threaded connector bore 144 mateable with coupling screw 242. With reference to FIG. 6, which is a simplified diagram of portions of connector 240, and in one embodiment, coupling screw 242 may be rotated into engagement with connector bore 144 by being rotated by a connector gear 246 meshed to an idler gear 248 rotating upon a hollow support shaft 250, meshed to a expansion drive gear 252, connected to a hollow shaft 254 extending through or along extension shaft 202, terminating near handle 210, and an actuator 206.

More particularly, as actuator 206 is rotated, an arrangement of gears or other linkage, not shown, but as would be understood within the art, within handle 210 causes a rotation of shaft 254. Drive gear 252 is rotated by input shaft 254 in engagement with intermediate idler gear 248, both gears being, for example, bevel gears. Idler gear 248 in turn drives connector gear 246, to rotate coupling screw 242 into connector bore 144. Connector 240 may be connected to implant 100, in this manner, either outside or inside the body.

Connector 240 further includes an expansion gear 260, configured to mesh with gear 128 of collar 120 or 120A, to cause an expansion or a reduction of a height of implant 100, inside or outside the body. In one embodiment, securing coupling screw 242 into connector bore 144 brings expansion gear 260 and collar gear 128 into mating engagement, and together with engagement extensions 244, promotes and maintains a proper alignment of gears 260 and 128 while the gears are subjected to a displacing force during rotation.

Expansion gear 260 meshes with a output gear 262 supported by shaft 264 in connection with transfer gear 266, which meshes with coupling drive gear 268 connected to input shaft 270, rotatable within hollow shaft 254. In use, gear 260 is rotated by first rotating actuator 208, connected to shaft 270 by gears or other means (not shown) within handle 210. Shaft 270 rotates drive gear 268, which rotates transfer gear 266, which rotates shaft 264, which rotates output gear 262, which rotates expansion gear 260. As expansion gear 260 is rotated, implant 100 increases or decreases height, as explained with respect to FIGS. 1-3, herein.

Figure 7:
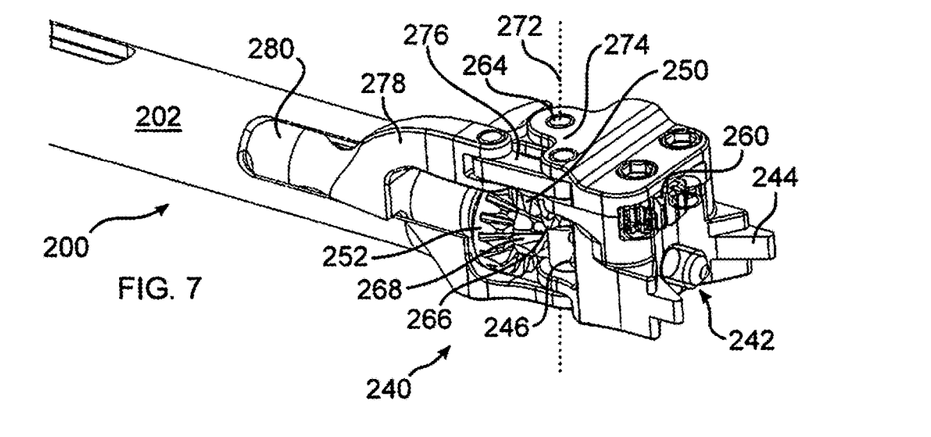
FIG. 7 depicts an enlarged view of a connector end of the tool of FIG. 4, showing an articulation arm for changing an angle of the connector end with respect to a remainder of the tool.
Figure 8:
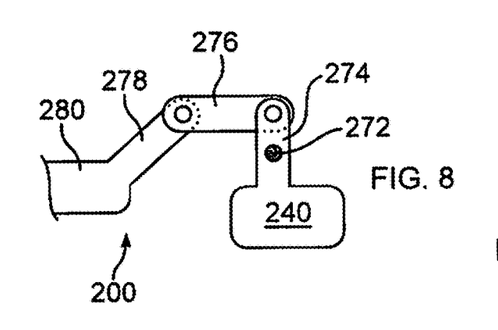
FIG. 8 is a schematic view of a first position of one configuration of the articulation of the connector of FIG. 7.
Figure 9:
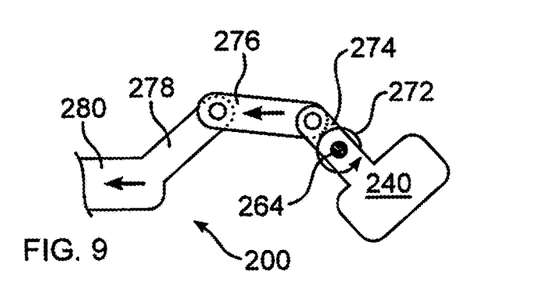
FIG. 9 is a schematic view of a second position of the configuration of FIG. 8.

With reference now to FIGS. 7-9, connector 240 may be articulated with respect to extension shaft 202. In this manner, tool 200 may form an elongate profile having a minimal width, to facilitate insertion into the body through, for example, a minimally invasive approach, in one embodiment through a shortened incision of less than about 5 cm, and in another embodiment through a shortened incision of about 3 cm, or may be inserted through a cannula. Once inside the body, connector 240 may be tilted or articulated within the body to align an attached implant 100 with a safe and effective insertion angle into a final implantation site, for example between vertebrae, past a removed portion of the disc annulus. In this manner, not only can an assembly of tool 200 and implant 100 have a narrower insertion profile, but an orientation of connector 240 and implant 100 may be changed after passing into the body, to align for insertion into a desired location, and to avoid delicate tissues, for example nerves or blood vessels, as implant 100 passes through body tissue into an implantation location.

Articulation of connector 240 may be carried out, in one embodiment, by pivoting connector 240 about a connector pivot axis 272. As diagrammatically illustrated in FIGS. 8-9, to maintain a proper alignment of drive gear 252, intermediate gear 248, and connector gear 246, as connector 240 is pivoted, pivot axis 272 is coaxially aligned with shaft 264, which may be extended to form a pivot pin. In one embodiment an articulation lever 274 extends from connector 240, and pivots about pivot axis 272. A link arm 276 is pivotally connected to lever 274 at one end, and to an articulation extension 278 at an opposite end. Articulation extension 278 is connected to an arm, shaft, or connecting tube 280 disposed within extension shaft 202. Tube 280 is threadably or otherwise connected to actuator 204, whereby a rotation of actuator 204 causes movement of tube 280, and link arm 276, either proximally or distally along a longitudinal axis defined by extension 202. Accordingly, articulation lever is pivoted about pivot axis 272, and connector 240 is angled with respect to extension shaft 202.

It should be understood that the linkages and pivot angle geometry shown in FIGS. 7-9 are exemplary, and may be configured to form a desired path through which connector 240 is moved when actuated by actuator 204. In accordance with another embodiment of the disclosure, any of articulation lever 274, link arm 276, articulation extension 278, and tube 280 can be omitted, and connector 240 can thereby pivot freely, or passively. Implant 100 can thereby be guided into position using body tissue as a guide, for example using the anterior annulus. To further reduce resistance to changing an orientation of connector 240 with respect to tool 200, gears 252, 268 may be disengaged from a remainder of connector 240, for example using a clutch, splined shaft, or other transmission (not shown).

In a further embodiment, lever 274, link arm 276, and or articulation extension 278 may be replaced with a biasing member (not shown), for example a spring, to urge connector 240 into a particular orientation, which may be altered by applying a force countering the biasing member. In a yet further embodiment, elements 274, 276, 278, and 280 are omitted, and connector 240 is non-pivotably affixed to extension shaft 202.

It should be understood that a selection of which gear actuator 204, 206, and 208 is configured to actuate which gear within connector 240 may be determined by a variety of factors, including an amount of torque to be applied.

Figure 10:
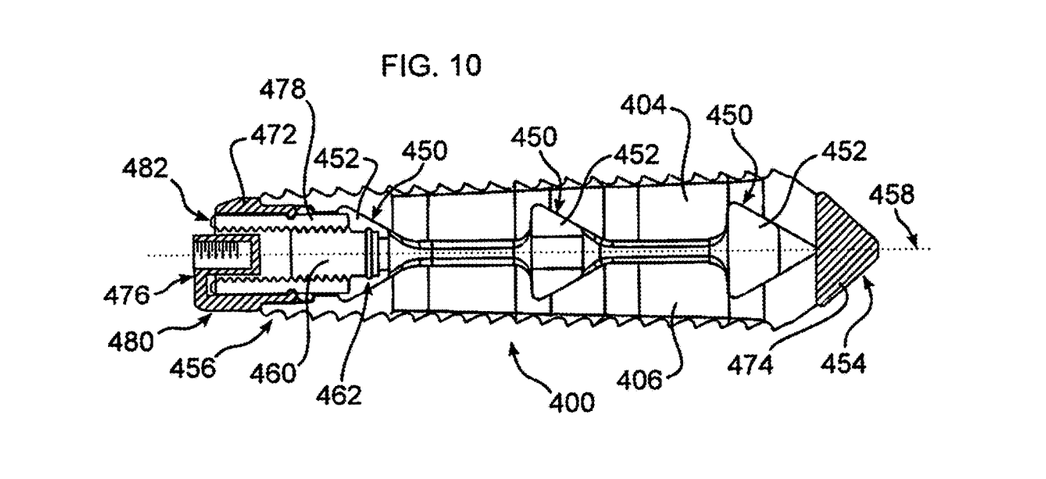
FIG. 10 is a cross-section through a center of an alternative spacer implant of the disclosure.

Turning now to FIG. 10, an alternative implant 400 is shown, in which endplates 404, 406 include expansion ramps 450, mateable with moveable lift ramps 452. Implant 400 forms a distal end 454 which is inserted first into the body, and a proximal end 456 to which a tool 200 may be connected, and between which a longitudinal axis 458 is defined. To expand implant 400, lift ramps 452 are displaced relative to endplates 404, 406, causing expansion ramps 450 to slide along lift ramps 452, thereby moving endplates 404, 406 relatively apart, thereby increasing a height of implant 400.

Lift ramps 452 are moveably connected in fixed alignment along longitudinal axis 458 to a threaded shaft 460 by an engagement flange 462. Rotation of shaft 460 causes lift ramps 452 to move distally or proximally along longitudinal axis 458 relative to expansion ramps 450 which are prevented from moving along longitudinal axis 458 by a frame stop 484, thereby causing an increase or decrease in a height of implant 400 transverse to longitudinal axis 458.

With further reference to FIG. 10, implant 400 is shown in bisected cross-section, in which a frame 480, shown in hatch fill, extends from a proximal frame end 472 to a distal frame end 474. Coupling screw 242 connects to a frame coupler 476, which is in turn connected to frame ends 472, 474 of implant 400. It should be understood that the particular manner and configuration of connecting coupler 476, and frame ends 472, 474 may be different than as a shown, however, in accordance with the disclosure, shaft 460 is moved forward or reverse along longitudinal axis 458 relative to frame 480, by threaded engagement with an internally threaded gear coupling sleeve 478, which rotates in fixed alignment along longitudinal axis 458.

Gear coupling sleeve 478 includes gear teeth 482 disposed about a circumference of a proximal end, which are engageable with expansion gear 260 when coupling screw 242 is coupled with frame coupler 476. While the connection between coupling screw 242 and frame coupler 476 is illustrated to be a threaded connection, other connection methods are possible, including a quick connect style releasable connection. When engaged with gear coupling sleeve 478, expansion gear 260 can be rotated as described with respect to the embodiment of FIGS. 1-3, to rotate gear coupling sleeve 478, to advance shaft 460, and cause expansion of endplates 404, 406.

Figure 11:
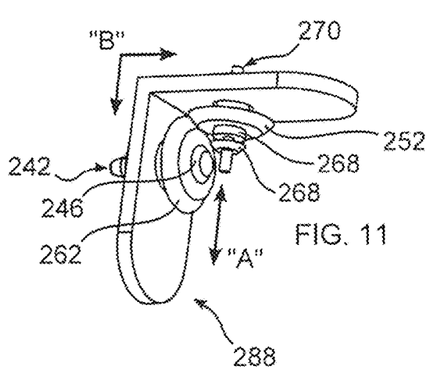
FIG. 11 depicts a front view of an alternative connector end of an implantation deployment tool of the disclosure.
Figure 12:
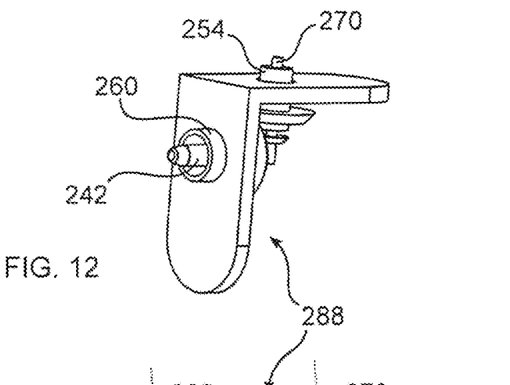
FIG. 12 depicts a back view of the connector end of FIG. 11.

An alternative tool end portion 288 of tool 200, useable with the implant embodiments of the disclosure, is diagrammatically illustrated in FIGS. 11-12. In this embodiment, transfer gear 266 and idler gear 248 are absent. Expansion drive gear 252 directly drives output gear 262, and coupling drive gear 268 directly drives connector gear 246. In this example, tool end frame 290 supports gears 252 and 268, at about 90 degrees with respect to gears 262 and 246. In this manner, a tool extending from frame 290 may be held by a practitioner at an angle with respect to an orientation of an implant of the disclosure, when inserted. By changing an angle of a bevel formed upon the gears, frame 290 may form a different angle "B" as needed, for example substantially greater or less than 90 degrees, which can facilitate insertion of an implant along a particular approach, for example an anterior, lateral, posterior, or an intermediate form of approach.

Figure 13:
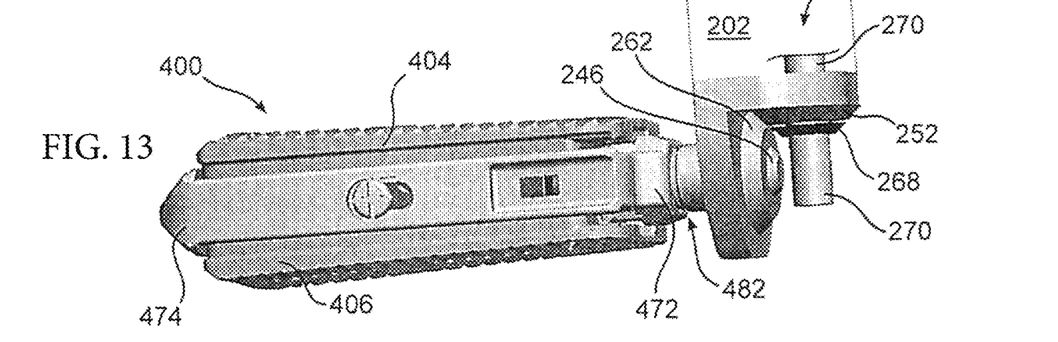
FIG. 13 depicts the implant of FIG. 10 connected to the connector end of FIG. 11.

FIGS. 11-12 additionally illustrate disengaging one or more gears, for example so that a single drive shaft may be used, or to avoid accidental movement of a gear. Arrow "A" indicates a direction of movement of shaft 270 which draws coupling drive gear 268 into or out of engagement with connector gear 246. Gear 252 may be alternatively, or additionally configured in this manner. Engagement splines (not shown) or a clutch 292, associated with shaft 270 in this example, can be used to enable a single shaft to operate a combination of one, two, or more gears, for example gears 252 or 268, depending upon an orientation of shaft 270 along direction "A". FIG. 13 illustrates implant 400 connected to tool end portion 288. In the embodiment shown, gear 268 is disengaged from gear 246, and endplates 404, 406 are at least partially expanded.

Figures 14, 15:
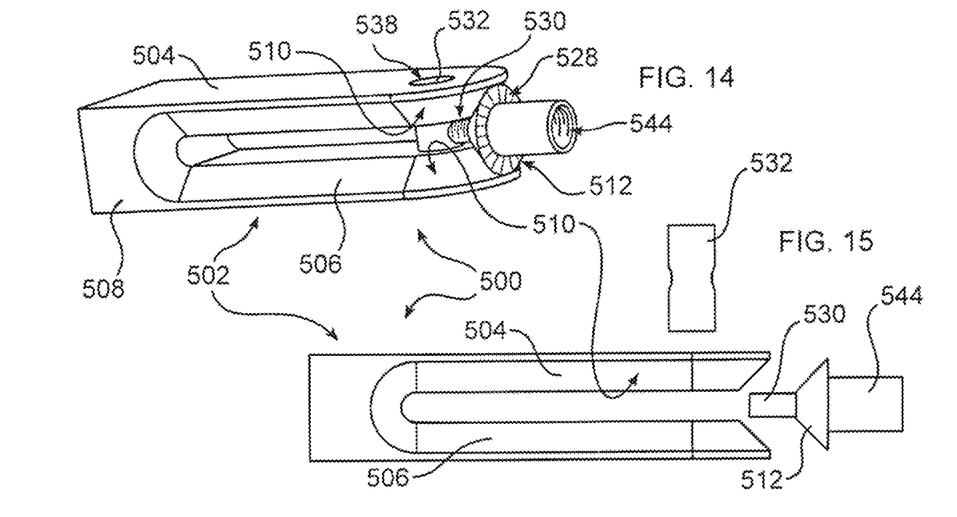
FIG. 14 depicts an alternative resilient form of a spacer implant in accordance with the disclosure.
FIG. 15 depicts an exploded view of the implant of FIG. 14.

Referring now to FIGS. 14-15, an alternative embodiment of the disclosure includes an implant 500 having a body 502 forming a base 508 from which extend two endplates 504, 506 connected at the base and bendable, at least, near base 508, and in one embodiment, along at least a portion of the length of at least one of endplates 504, 506. An interior profile of at least one of endplate 504, 506 includes a ramped surface 510. A cone 512 is driveable into engagement with one or both ramped surfaces 510, to thereby force endplates 504, 506 to bend, and to thereby increase a height of implant 500. This embodiment enables passive articulation over a wide range of angles, for example at least about 90 degrees of articulation, although substantially more or less range is achievable. Additionally, once cone 512 is driven sufficiently into engagement with ramped surface 510, an angle of articulation can be affixed due to friction between cone 512 and surface 510, facilitating implantation. Reversal of cone 512 out of engagement with ramped surface 510 can restore free, passive articulation.

In one embodiment, tool 200 can be used with implant 500 as described herein with respect to implants 100 and 400. More particularly, coupling screw is engaged with threaded connector bore 544 to releaseably secure tool 200 to implant 500. Expansion gear 528 then couples with output gear 260 which can rotate cone 512. In one embodiment, cone 512 is threadably engaged with cone support rod 530, which is connected to a pin 532 secured to endplates 504, 506. As cone 512 is threaded further onto rod 530 through rotation by output gear 260, cone 512 is advanced along ramps 510 to force apart endplates 504, 506, expanding implant 500. In another embodiment, rod 530 threads into pin 532 and cone 512 is affixed to rod 530. Accordingly, rotation of cone 512 causes rod 530 to advance further into pin 532, drawing cone 512 along ramps 510, expanding implant 500. Pin 532 can slide within a bore 534 in endplates 504, 506 as the latter move during expansion.

If endplates 504, 506 and or base 508 are resilient, they may bend back when cone 512 is withdrawn, returning implant 500 to a former, reduced height profile, for example for removal or repositioning. Accordingly, endplates 504, 506 and or base 508 can be fabricated from a polymeric material, a naturally resilient material, or a resilient metal, for example a shape memory alloy, or any other resilient biocompatible material of sufficient strength and durability for separating bones within the body.

If endplates 504, 506 expand more on one side of implant 500 than another, correction of lordosis and restoration of disc height can be accomplished together in a single expansion of implant 500. However, in some circumstances, it may be therapeutically advantageous for an implant as described for FIGS. 14-15 to expand about evenly along a linear dimension, or to expand to a predetermined extent at each end.

Figure 16:
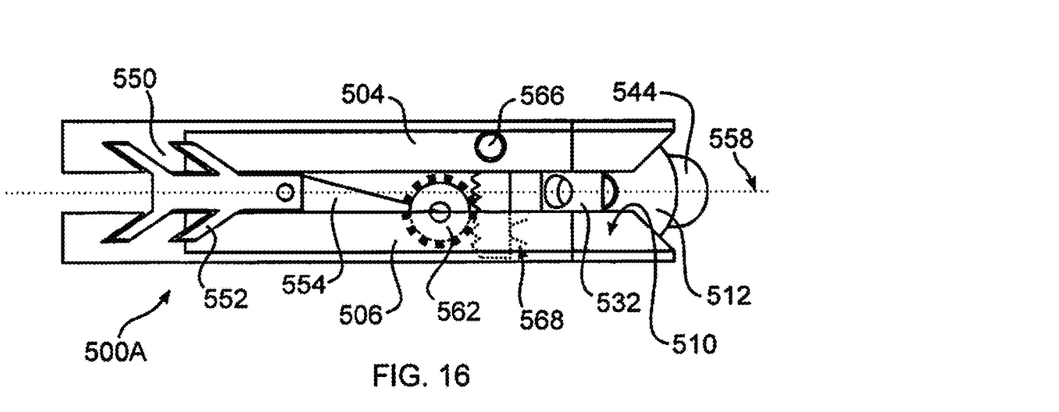
FIG. 16 depicts an alternative spacer implant in accordance with the disclosure, including resilient and gear driven expansion elements.
Figure 17:
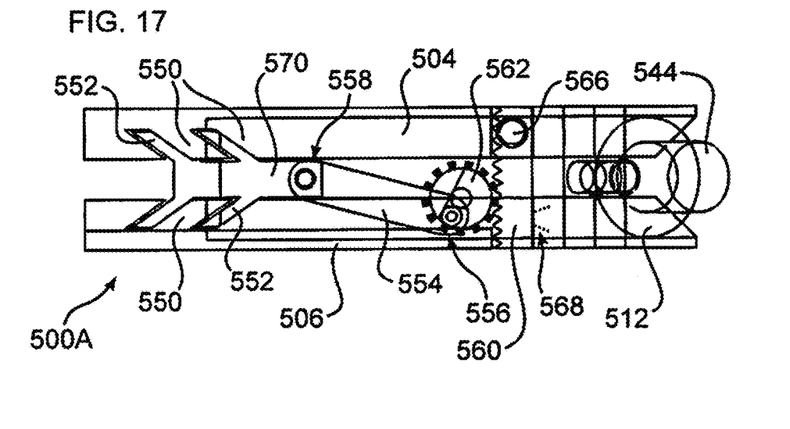
FIG. 17 is a cross-section through a center of the implant of FIG. 16.
Figure 18:
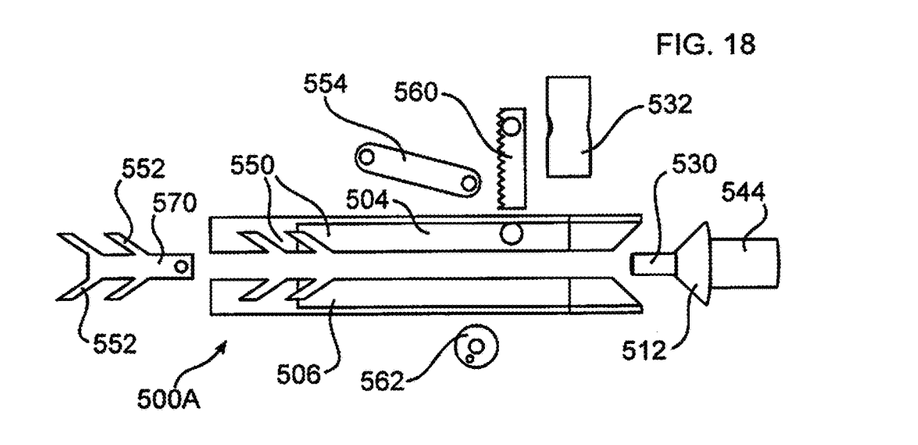
FIG. 18 is an exploded view of the implant of FIG. 16.

Accordingly, with reference to FIGS. 16-18, implant 500A is similar to implant 500 with the following distinctions. As endplates 504, 506 are separated by movement of cone 512 along ramps 510, a gear rack 560, affixed to one of endplate 504, 506 is displaced along an axis transverse to a longitudinal axis 558 of implant 500. Gear rack 560 meshes with a pinion 562 rotatably connected to the other of endplate 504, 506 to which gear rack 560 is affixed. In this manner, as endplates 504, 506 separate relative to each other at one end thereof, pinion 562 is caused to rotate by rack 560. A strut 554 is eccentrically pivotally mounted to pinion 562 at a proximal end 556, and pivotally mounted to a ramp carriage 570 at a distal end 558. As pinion 562 rotates, strut distal end 558 is moved forwards or backwards along longitudinal axis 558, drawing ramp carriage 570 forwards or backwards along longitudinal axis 558. Gear rack 560 can have a pivotal mount 566 to an endplate 504, and can be supported by a guide 568 within an opposite endplate 506, to maintain a correct meshing alignment with pinion 562 as endplates 504, 506 displace relative to each other.

Extending from ramp carriage 570 to move along longitudinal axis 558 therewith, are one or more lift ramps 552, which function substantially as described with respect to implant 400 of FIG. 10. More particularly, lift ramps 552 engage expansion ramps 550 of endplates 504, 506, such that as ramp carriage 570 is drawn along longitudinal axis 558 in a proximal direction, towards cone 512, expansion ramps 550 slide along lift ramps 552 and endplates 504, 506 separate relative to each other, increasing a height of implant 500 in a direction transverse to longitudinal axis 558. Gearing of rack 560 and pinion 562, and an angle of cone 512 and ramped surface 510, are selected to cause expansion of a distal end of implant 500 at the same rate, or a different rate, than expansion of a proximal end of implant 500, due to movement of cone 512 along ramped surface 510.

In accordance with the disclosure, during implantation of intervertebral spacers from a posterior approach, there is a need to avoid damaging nerve roots. A prior art spacer dimensioned to separate bones can block a view of nerve roots as it is inserted, and due to its large size, poses a greater risk of contacting nerve roots during insertion into the body. As a result, the medical practitioner must more often retract nerve roots, with attendant danger of tissue damage. Implants 100, 400, 500 of the disclosure form a smaller dimension during implantation relative to a final dimension for spacing bones. Accordingly, nerve roots can be visualized and avoided during insertion, and nerve root manipulation can be avoided or minimized. Further, in cooperation with tool 200, implants of the disclosure can be articulated with respect to an insertion tool during implantation, enabling exceptional anterior placement without impaction, as well as facilitating implantation from other approaches. Further, implants of the disclosure provide superior lordosis correction with respect to prior art implants, as a final dimension is adjustable at each end of the implant. Implants of the disclosure further develop a good bone contact area, as an implant with a larger footprint may be inserted through a reduced size incision, due to the overall dimensions of the implant being reduced during insertion.

The disclosure enables coupling expandable implants 100, 400, 500 with an articulating insertion instrument 200, which can provide a driving force at any desired angle.

Implants 100, 400, 500 of the disclosure enable a continuous expansion and retraction over a range of displacements according to predetermined dimensions of a specific spacer design. This provides the ability to distract vertebral bodies or other bones to a desired height or separation. Implants 100, 400, 500 may also be collapse to a reduced height for repositioning or removal, if therapeutically advantageous for the patient.

Endplates 104,106, 404,406, 504,506 may be shaped to form planes or surfaces which converge relative to each, to provide for proper lordosis, and can be provided with openings through which bone may grow, and into which bone graft material may be placed. Implant spacers 100, 400, 500 of the disclosure may be used to distract, or force bones of a joint apart, or may be used to maintain a separation of bones created by other means, for example by a retractor. Endplates may additionally be curved to conform to the surface of body tissue, for example the surface of cortical bone, of the vertebra to be contacted, for improved fixation and load bearing.

Implants of the disclosure may be fabricated using any biocompatible materials known to one skilled in the art, having sufficient strength, flexibility, resiliency, and durability for the patient, and for the term during which the device is to be implanted. Examples include but are not limited to metal, such as, for example titanium and chromium alloys; polymers, including for example, PEEK or high molecular weight polyethylene (HMWPE); and ceramics. There are many other biocompatible materials which may be used, including other plastics and metals, as well as fabrication using living or preserved tissue, including autograft, allograft, and xenograft material.

Portions or all of the implant may be radiopaque or radiolucent, or materials having such properties may be added or incorporated into the implant to improve imaging of the device during and after implantation.

Implants 100, 400, 500 may be formed using titanium, or a cobalt-chrome-molybdenum alloy, Co—Cr—Mo, for example as specified in ASTM F1537 (and ISO 5832-12). The smooth surfaces may be plasma sprayed with commercially pure titanium, as specified in ASTM F1580, F1978, F1147 and C-633 (and ISO 5832-2). Alternatively, part or all of implants 100, 400, 500 may be formed with a polymer, for example ultra-high molecular weight polyethylene, UHMWPE, for example as specified in ASTM F648 (and ISO 5834-2). In one embodiment, PEEK-OPTIMA (a trademark of Invibio Ltd Corp, United Kingdom) may be used for one or more components of the implants of the disclosure. For example, polymeric portions can be formed with PEEK-OPTIMA, which is radiolucent, whereby bony ingrowth may be observed. Other polymeric materials with suitable flexibility, durability, and biocompatibility may also be used.

In accordance with the invention, implants of various sizes may be provided to best fit the anatomy of the patient. Components of matching or divergent sizes may be assembled during the implantation procedure by a medical practitioner as best meets the therapeutic needs of the patient, the assembly inserted within the body using an insertion tool. Implants of the invention may also be provided with an overall angular geometry, for example an angular mating disposition of endplates, to provide for a natural lordosis, or a corrective lordosis, for example of from 0° to 6° for a cervical application, although much different values may be advantageous for other joints. Lordotic angles may also be formed by shaping one or both endplates to have relatively non-coplanar surfaces.

Expanded implant heights, for use in the cervical vertebrae for example, may typically range from 7 mm to 12 mm, but may be larger or smaller, including as small as 5 mm, and as large as 16 mm, although the size is dependent on the patient, and the joint into which an implant of the invention is to be implanted. Implants 100, 400, 500 may be implanted within any level of the spine, and may also be implanted in other joints of the body, including joints of the hand, wrist, elbow, shoulder, hip, knee, ankle, or foot.

In accordance with the invention, a single implant 100, 400, 500 may be used, to provide stabilization for a weakened joint or joint portion. Alternatively, a combination of two, three, or more of any of implants 100, 400, 500 may be used, at a single joint level, or in multiple joints. Moreover, implants of the disclosure may be combined with other stabilizing means.

Additionally, implants of the disclosure may be fabricated using material that biodegrades in the body during a therapeutically advantageous time interval, for example after sufficient bone ingrowth has taken place. Further, implants of the disclosure are advantageously provided with smooth and or rounded exterior surfaces, which reduce a potential for deleterious mechanical effects on neighboring tissues.

Any surface or component of an implant of the disclosure may be coated with or impregnated with therapeutic agents, including bone growth, healing, antimicrobial, or drug materials, which may be released at a therapeutic rate, using methods known to those skilled in the art.

Devices of the disclosure provide for adjacent vertebrae to be supported during flexion/extension, lateral bending, and axial rotation. In one embodiment, implant 100, 400, or 500 is indicated for spinal arthroplasty in treating skeletally mature patients with degenerative disc disease, primary or recurrent disc herniation, spinal stenosis, or spondylosis in the lumbosacral spine (LI-SI). Degenerative disc disease is advantageously defined as discogenic back pain with degeneration of the disc confirmed by patient history and radiographic studies, with or without leg (radicular) pain. Patients are advantageously treated, for example, who may have spondylolisthesis up to Grade 1 at the involved level. The surgery position spacer 100 may be performed through an Anterior, Anterolateral, Posterolateral, and/or Lateral approach.

In a typical embodiment, implants of the disclosure have an uncompressed height, before insertion, of 12 to 18 mm, and may advantageously be provided in cross-sections of 23×32 mm, 26×38 mm and 26×42 mm, with 4, 8, 12, or 16 degree lordotic angles, although these are only representative sizes, and substantially smaller or larger sizes can be therapeutically beneficial. In one embodiment implants in accordance with the instant disclosure are sized to be inserted using an MIS approach (a reduced incision size, for example less than about 5 cm, and advantageously less than about 2.5 cm, with fewer and shorter cuts through body tissue). Implants 100, 400, 500 may advantageously be used in combination with other known or hereinafter developed forms of stabilization or fixation, including for example rods and plates.

All references cited herein are expressly incorporated by reference in their entirety. There are many different features to the present invention and it is contemplated that these features may be used together or separately. Unless mention was made above to the contrary, it should be noted that all of the accompanying drawings are not to scale. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. An implant for separating bones of a joint, the implant comprising:
    a base at a distal end of the implant;
    an upper endplate extending from the base and configured to engage a first vertebral body;
    a lower endplate extending from the base and configured to engage a second vertebral body;
    a cone disposed between the upper endplate and the lower endplate at a proximal end of the implant and configured to bend each of the upper endplate and the lower endplate to increase a height of the implant,
    wherein an insertion tool engages the implant at the proximal end of the implant
    wherein a coupling screw is engaged with a threaded connector bore to releasably secure the insertion tool to the implant,
    wherein an expansion gear is coupled with an output gear configured to rotate the cone, and the cone is threadedly engaged with a cone support rod, which is coupled to a pin secured to the upper and lower endplates.

2. The implant of claim 1, wherein the cone engages a ramped surface of each of the upper endplate and the lower endplate.

3. The implant of claim 1, further including at least one ramped surface formed upon at least one of the upper endplate and the lower endplate, said at least one ramped surface mateable with the cone to be resiliently displaced to change a height dimension of said implant when said cone is moved against said at least one ramped surface.

4. The implant of claim 1, wherein the upper endplate and the lower endplate are configured to bend back to an original configuration when the cone is withdrawn to decrease the height of the implant.

5. The implant of claim 4, wherein the threaded connecting bore is engaged with the cone.

6. The implant of claim 5, wherein the insertion tool includes the coupling screw and the output gear.

7. An implant for separating bones of a joint, the implant comprising:
    a base at a distal end of the implant;
    an upper endplate extending from the base and configured to engage a first vertebral body;
    a lower endplate extending from the base and configured to engage a second vertebral body;
    a cone disposed between the upper endplate and the lower endplate at a proximal end of the implant and configured to bend each of the upper endplate and the lower endplate to increase a height of the implant; and
    wherein a coupling screw is engaged with a threaded connector bore to releasably secure an insertion tool to the implant,
    wherein an expansion gear is coupled with an output gear configured to rotate the cone, and the cone is threadedly engaged with a cone support rod, which is coupled to a pin secured to the upper and lower endplates,
    wherein the insertion tool includes the output gear and engages the expansion gear at the proximal end of the implant.

8. The implant of claim 7, wherein the cone engages a ramped surface of each of the upper endplate and the lower endplate.

9. The implant of claim 7, further including at least one ramped surface formed upon at least one of the upper endplate and the lower endplate, said at least one ramped surface mateable with the cone to be resiliently displaced to change a height dimension of said implant when said cone is moved against said at least one ramped surface.

10. The implant of claim 7, wherein the upper endplate and the lower endplate are configured to bend back to an original configuration when the cone is withdrawn to decrease the height of the implant.

11. The implant of claim 10, wherein the threaded connecting bore is engaged with the cone.

* * * * *